(12) United States Patent
Park et al.

(10) Patent No.: US 10,217,680 B2
(45) Date of Patent: Feb. 26, 2019

(54) TEST APPARATUS AND MANUFACTURING APPARATUS OF LIGHT EMITTING DEVICE PACKAGE

(71) Applicant: Samsung Electronics Co., Ltd., Suwon-si (KR)

(72) Inventors: Dae Seo Park, Suwon-si (KR); Song Ho Jeong, Hwaseong-si (KR); Oh Seok Kwon, Hwaseong-si (KR); Jong Tae Kim, Hwaseong-si (KR); Choo Ho Kim, Yongin-si (KR)

(73) Assignee: SAMSUNG ELECTRONICS CO., LTD., Gyeonggi-do (KR)

( * ) Notice: Subject to any disclaimer, the term of this patent is extended or adjusted under 35 U.S.C. 154(b) by 71 days.

(21) Appl. No.: 15/403,330

(22) Filed: Jan. 11, 2017

(65) Prior Publication Data

US 2018/0040519 A1 Feb. 8, 2018

(30) Foreign Application Priority Data

Aug. 3, 2016 (KR) .......................... 10-2016-0099086

(51) Int. Cl.
| | | |
|---|---|---|
| *G06K 9/00* | (2006.01) | |
| *H01L 21/66* | (2006.01) | |
| *G01N 21/64* | (2006.01) | |
| *G01N 21/95* | (2006.01) | |
| *H01L 33/56* | (2010.01) | |

(52) U.S. Cl.
CPC ............. *H01L 22/24* (2013.01); *G01N 21/64* (2013.01); *G01N 21/95* (2013.01); *H01L 33/56* (2013.01); *G01N 2201/062* (2013.01); *H01L 2933/0033* (2013.01)

(58) Field of Classification Search
None
See application file for complete search history.

(56) References Cited

U.S. PATENT DOCUMENTS

| | | | |
|---|---|---|---|
| 6,372,608 B1 | 4/2002 | Shimoda et al. |
| 6,645,830 B2 | 11/2003 | Shimoda et al. |
| RE38,466 E | 3/2004 | Inoue et al. |
| 6,818,465 B2 | 11/2004 | Biwa et al. |
| 6,818,530 B2 | 11/2004 | Shimoda et al. |
| 6,858,081 B2 | 2/2005 | Biwa et al. |
| 6,967,353 B2 | 11/2005 | Suzuki et al. |
| 7,002,182 B2 | 2/2006 | Okuyama et al. |
| 7,084,420 B2 | 8/2006 | Kim et al. |
| 7,087,932 B2 | 8/2006 | Okayama et al. |
| 7,154,124 B2 | 12/2006 | Han et al. |

(Continued)

FOREIGN PATENT DOCUMENTS

| | | |
|---|---|---|
| JP | 2010204051 A * | 9/2010 |
| JP | 2012-098209 | 11/2010 |

(Continued)

*Primary Examiner* — Delomia L Gilliard
(74) *Attorney, Agent, or Firm* — Muir Patent Law, PLLC

(57) ABSTRACT

A test apparatus includes a lighting unit radiating light on a to-be-tested object having a light transmitting resin containing a light conversion material; a camera unit obtaining an image of the to-be-tested object while the light transmitting resin is emitted by receiving light emitted by the lighting unit; and a controller determining whether the to-be-tested object is defective by calculating gray values from the image obtained by the camera unit.

20 Claims, 9 Drawing Sheets

(56) References Cited

U.S. PATENT DOCUMENTS

| | | |
|---|---|---|
| 7,208,725 B2 | 4/2007 | Sherrer et al. |
| 7,288,758 B2 | 10/2007 | Sherrer et al. |
| 7,319,044 B2 | 1/2008 | Han et al. |
| 7,449,213 B2 | 11/2008 | Yokono et al. |
| 7,501,656 B2 | 3/2009 | Han et al. |
| 7,709,857 B2 | 5/2010 | Kim et al. |
| 7,759,140 B2 | 7/2010 | Lee et al. |
| 7,781,727 B2 | 8/2010 | Sherrer et al. |
| 7,790,482 B2 | 9/2010 | Han et al. |
| 7,940,350 B2 | 5/2011 | Jeong |
| 7,959,312 B2 | 6/2011 | Yoo et al. |
| 7,964,881 B2 | 6/2011 | Choi et al. |
| 7,985,976 B2 | 7/2011 | Choi et al. |
| 7,994,525 B2 | 8/2011 | Lee et al. |
| 8,008,683 B2 | 8/2011 | Choi et al. |
| 8,013,352 B2 | 9/2011 | Lee et al. |
| 8,049,161 B2 | 11/2011 | Sherrer et al. |
| 8,129,711 B2 | 3/2012 | Kang et al. |
| 8,179,938 B2 | 5/2012 | Kim |
| 8,263,987 B2 | 9/2012 | Choi et al. |
| 8,324,646 B2 | 12/2012 | Lee et al. |
| 8,399,944 B2 | 3/2013 | Kwak et al. |
| 8,432,511 B2 | 4/2013 | Jeong |
| 8,459,832 B2 | 6/2013 | Kim |
| 8,502,242 B2 | 8/2013 | Kim |
| 8,525,217 B2 * | 9/2013 | Nishiwaki ........... H01L 33/0095 118/696 |
| 8,536,604 B2 | 9/2013 | Kwak et al. |
| 8,735,931 B2 | 5/2014 | Han et al. |
| 8,766,295 B2 | 7/2014 | Kim |
| 8,922,643 B2 | 12/2014 | Ji et al. |
| 2010/0214345 A1* | 8/2010 | Saita ................... B41J 2/0451 347/19 |
| 2012/0190136 A1 | 7/2012 | Hong |
| 2015/0364644 A1* | 12/2015 | Yoshida ................ C09K 11/02 438/16 |
| 2015/0375498 A1* | 12/2015 | Horikawa ........... B41J 2/16579 347/14 |
| 2016/0020155 A1* | 1/2016 | Kim .................. G01R 31/2635 438/16 |
| 2016/0133805 A1 | 5/2016 | Park et al. |

FOREIGN PATENT DOCUMENTS

| | | | |
|---|---|---|---|
| JP | 2011095008 A * | 5/2011 | |
| JP | 2014-003093 | 1/2014 | |
| KR | 2009-0030674 A | 3/2009 | |
| KR | 1059232 B1 | 8/2011 | |
| KR | 1102043 B1 | 12/2011 | |
| KR | 2012-0086443 | 8/2012 | |
| KR | 2013-0130567 A | 12/2013 | |
| KR | 2014-0111082 A | 9/2014 | |
| KR | 1472444 B1 | 12/2014 | |
| KR | 1593799 B1 | 2/2016 | |
| WO | WO 2015027527 A1 * | 3/2015 | ........... G01N 21/954 |

\* cited by examiner

P Rank
GV : 66

R Rank
GV : 94

T Rank
GV : 110

U Rank
GV : 143

TEST APPARATUS AND MANUFACTURING APPARATUS OF LIGHT EMITTING DEVICE PACKAGE

CROSS-REFERENCE TO RELATED APPLICATION

This application claims benefit of priority under 35 U.S.C. § 119 to Korean Patent Application No. 10-2016-0099086, filed on Aug. 3, 2016, in the Korean Intellectual Property Office, the disclosure of which is incorporated herein by reference in its entirety.

BACKGROUND

1. Field

The present disclosure relates to a test apparatus and a manufacturing apparatus of a light emitting device package.

2. Description of Related Art

As semiconductor light emitting devices, light emitting diodes (LEDs) have advantages, such as relatively low power consumption, a relatively long lifespan, and the ability to implement light of various colors, as compared to light sources of the related art, such as fluorescent lamps and incandescent lamps. Based on such advantages, the application of LEDs extends to various types of lighting devices, and to the backlight units of display devices, and vehicle headlamps. LEDs may be mounted within certain package bodies in light emitting device package forms, and light emitting device packages may include light transmitting resins containing light conversion materials in order to adjust colors of light and protect LEDs.

SUMMARY

In some embodiments, the disclosure is directed to a method of testing an object, comprising: radiating light from a lighting unit to a test object having a light transmitting resin containing a light conversion material; obtaining an image of the test object by a camera unit while the light transmitting resin is receiving light emitted by the lighting unit; and determining whether the test object is defective by calculating gray values corresponding to the image obtained by the camera unit.

In some embodiments, the disclosure is directed to a method of manufacturing comprising: providing a light emitting device package; dispensing a light transmitting resin containing a light conversion material to the light emitting device package; and obtaining an image by radiating light having a certain wavelength onto the light emitting device package having the light transmitting resin dispensed thereon; calculating gray values from the obtained image; comparing the calculated gray values with a reference range of gray values set according to a rank of the light emitting device package; and determining whether the light emitting device package is defective based on the comparing of the calculated gray values with the reference range of gray values.

In some embodiments, the disclosure is directed to a method for testing comprising: radiating light to an object having a light transmitting resin containing a light conversion material; obtaining an image of the object while the light conversion material is excited by the light radiated by the lighting unit; calculating at least one gray value corresponding to the image; comparing the at least one gray value with a reference range of gray values set according to a rank of the object; and determining whether the at least one gray value is within the reference range of gray values.

BRIEF DESCRIPTION OF DRAWINGS

The above, and other aspects, features, and advantages of the present disclosure will be more clearly understood from the following detailed description when taken in conjunction with the accompanying drawings, in which.

DETAILED DESCRIPTION

Figure 1:
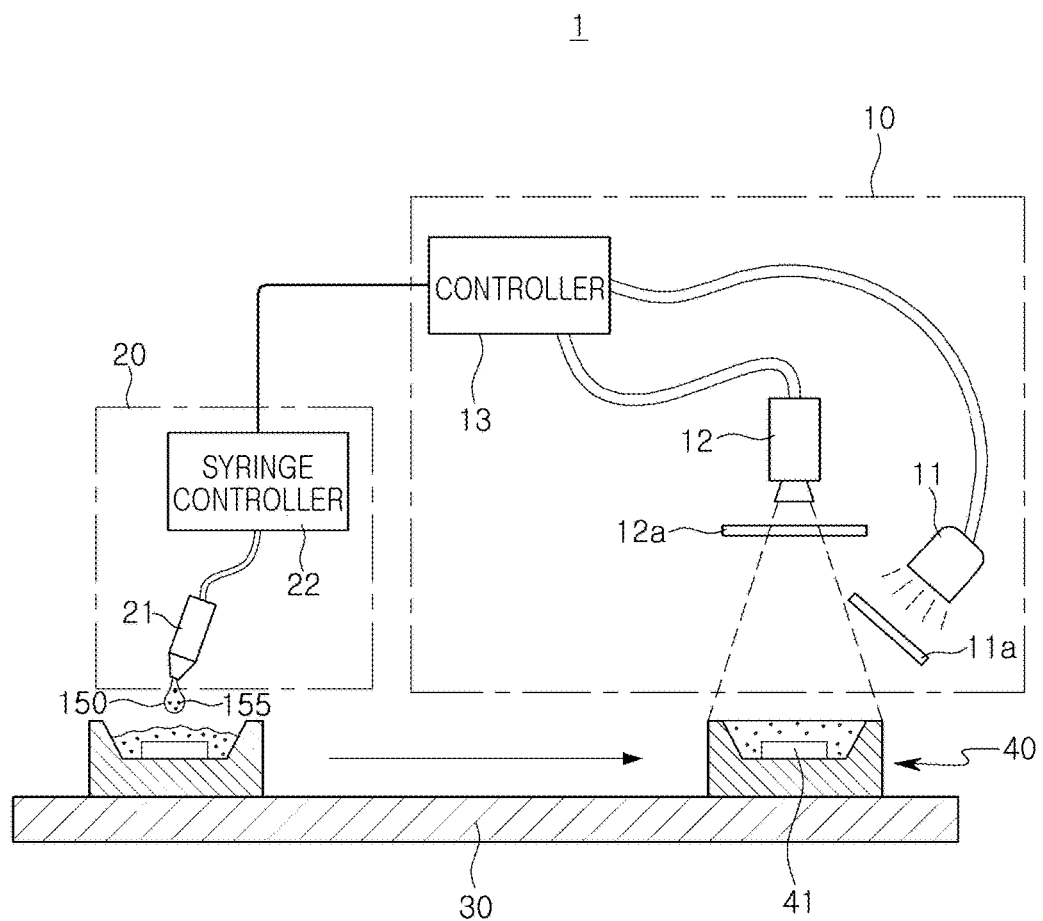
FIG. 1 is a diagram of a manufacturing apparatus for manufacturing a light emitting device package according to an example embodiment.

In the disclosure, it will be understood that when an element is referred to as being "connected" or "coupled" to, or "on" another element, it can be directly connected or coupled to, or on the other element or intervening elements may be present. In contrast, when an element is referred to as being "directly connected," "directly coupled," in or "directly on" to another element, there are no intervening elements present. Other words used to describe the relationship between elements should be interpreted in alike fashion (e.g., "between" versus "directly between," "adjacent" versus "directly adjacent," etc.). However, the term "contact," as used herein refers to a direct connection (i.e., touching) unless the context indicates otherwise.

As is traditional in the field of the disclosed technology, features and embodiments are described, and illustrated in the drawings, in terms of functional blocks, units and/or modules. Those skilled in the art will appreciate that these blocks, units and/or modules are physically implemented by electronic (or optical) circuits such as logic circuits, discrete components, microprocessors, hard-wired circuits, memory elements, wiring connections, and the like, which may be formed using semiconductor-based fabrication techniques or other manufacturing technologies. In the case of the blocks, units and/or modules being implemented by microprocessors or the like, they may be programmed using software (e.g., microcode) to perform various functions discussed herein and may optionally be driven by firmware and/or software. Alternatively, each block, unit and/or module may be implemented by dedicated hardware, or as a combination of dedicated hardware to perform some functions and a processor (e.g., one or more programmed microprocessors and associated circuitry) to perform other functions. Also, each block, unit and/or module of the embodiments may be physically separated into two or more interacting and discrete blocks, units and/or modules without departing from the scope of the inventive concepts. Further, the blocks, units and/or modules of the embodiments may be physically combined into more complex blocks, units and/or modules without departing from the scope of the inventive concepts.

Terms such as "uniform," "same," "equal," "planar," or "coplanar," as used herein when referring to orientation, layout, location, shapes, sizes, amounts, or other measures do not necessarily mean an exactly identical orientation, layout, location, shape, size, amount, or other measure, but are intended to encompass nearly identical orientation, layout, location, shapes, sizes, amounts, or other measures within acceptable variations that may occur, for example, due to manufacturing processes. The term "substantially" may be used herein to emphasize this meaning, unless the context or other statements indicate otherwise. For example, items described as "substantially uniform," "substantially the same," "substantially equal," or "substantially planar," may be exactly the same, equal, or planar, or may be the same, equal, or planar within acceptable variations that may occur, for example, due to manufacturing processes.

FIG. 1 is a diagram of a manufacturing apparatus for manufacturing a light emitting device package according to an example embodiment.

Referring to FIG. 1, a manufacturing apparatus 1 for manufacturing a light emitting device package according to an example embodiment may include a resin dispensing unit 20, dispensing a light transmitting resin 150 to a light emitting device package 40, and a jig 30 allowing the light emitting device package 40 to be seated thereon.

The light transmitting resin 150, dispensed to the light emitting device package 40, may include a light conversion material 155, adjusting colors of light output by a light emitting device 41. The light conversion material 155 may be, for example, a phosphor emitting light having a different wavelength than light emitted by the light emitting device 41, after being excited thereby.

The resin dispensing unit 20 may include a syringe 21, dispensing the light transmitting resin 150 containing the light conversion material 155 in dot units, and a syringe control unit (e.g., controller) 22. For example, the resin dispensing unit 20 may disburse droplets of the light transmitting resin 150 one-by-one using the syringe 21.

A test apparatus 10 may test the light transmitting resin 150 containing the light conversion material 155 that has been dispensed to the light emitting device package 40. For example, the test apparatus 10 may determine whether the light transmitting resin 150, containing the light conversion material 155, is abnormal by using the light emitting device package 40 having the light emitting device 41, encapsulated by the light transmitting resin 150 containing the light conversion material 155, as a to-be-tested object (also referred to herein as a "test object"). A light transmitting resin 150 containing the light conversion material 155 may be determined to be abnormal when, for example, a ratio of the light conversion material 155 to the light transmitting resin 150 is determined to be different from an expected or desired ratio. The test apparatus 10 may radiate light to the light emitting device package 40 by using a lighting unit 11, obtain an image of the light emitting device package 40 by using a camera unit 12, and determine whether the to-be-tested object (e.g., the light emitting device package 40) is defective by using a control unit (e.g., test controller 13).

The lighting unit 11 may have a light source emitting light having a certain wavelength. In example embodiments, the lighting unit 11 may include an ultraviolet (UV) light emitting diode (LED) or a blue LED as a light source. The wavelength of light emitted by the lighting unit 11 may be substantially equal to or shorter than that of light emitted by the light emitting device 41 that is included in the light emitting device package 40.

The camera unit 12 may capture an image of the light emitting device package 40. The image generated by the camera unit 12 may be obtained by capturing an image of an upper surface of the light emitting device package 40 coated with the light transmitting resin 150 containing the light conversion material 155.

The controller 13 may control operations of the lighting unit 11 and the camera unit 12, and may calculate gray values from the image generated by the camera unit 12. The controller 13 may determine whether the light transmitting resin 150, containing the light conversion material 155, is abnormal, based on the calculated gray values. The controller 13 may also determine whether the light emitting device package 40 is defective. In some embodiments, the light emitting device package 40 may be determined to be defective when, for example, the light transmitting resin 150, containing the light conversion material 155, is determined to be abnormal.

When the gray values calculated from the image generated by the camera unit 12 are outside of a reference range, the test controller 13 may determine whether the mixing ratio of the light conversion material 155 contained in the light transmitting resin 150 is abnormal. In some embodiments, the mixing ratio of the light conversion material 155 contained in the light transmitting resin 150 may be determined to be abnormal when the ratio exceeds a reference value or range of values. For example, when the light emitting device package 40 is divided into a P rank, a R rank, a T rank, and a U rank, according to a difference of the mixing ratio of the light conversion material 155 contained in the light transmitting resin 150, the reference range may include reference gray values contained by the light emitting device package 40 of each rank.

In an example embodiment, the test apparatus 10 and the resin dispensing unit 20 may be provided as a single device. For example, the test apparatus 10 may be combined with a device for performing a process of dispensing the light transmitting resin 150 onto the light emitting device package 40, such that the test apparatus 10 and the device may be provided as a single device. The test controller 13 and the syringe controller 22 may be integrated as a single control module. In some embodiments, the determinations performed by the test apparatus and the test controller 13 may be computer-automated determinations.

Figure 2:
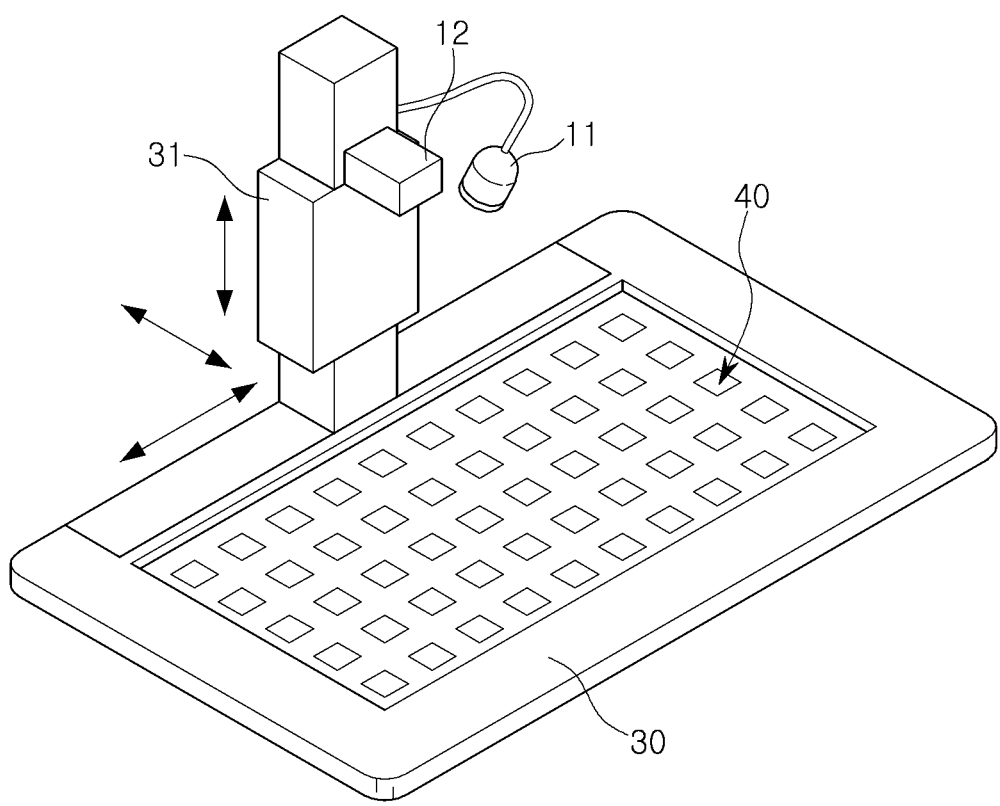
FIG. 2 is a perspective view illustrating the exterior of a test apparatus for testing a light emitting device package according to an example embodiment.

FIG. 2 is a perspective view of a test apparatus for testing a light emitting device package according to an example embodiment.

Referring to FIG. 2, a testing apparatus 10, according to an example embodiment, may include a lighting unit 11, a camera unit 12, and a test controller 13. The test controller 13, illustrated in FIG. 1, may be mounted in a housing (not illustrated) of the test apparatus 10 so as not to be exposed externally.

Light emitting device packages 40 may be arranged in an array in a jig 30. For example, the light emitting device packages 40 may be disposed in a plurality of rows and columns to be seated within the jig 30. The lighting unit 11 and the camera unit 12 may be coupled to a supporting portion 31 so as to move up and down or right and left. The lighting unit 11 and the camera unit 12 may inspect the respective light emitting device packages 40 while moving in accordance with the rows and columns in which the light emitting device packages 40 are arranged.

In some embodiments, the lighting unit 11 and the camera unit 12 may have, for example, a second optical system, such as a UV filter 11a, a color filter 12a, etc. (refer to FIG. 1).

The lighting unit 11 may include an ultraviolet (UV) LED emitting light having a certain wavelength, for example, a UV ray, as a light source, and may simultaneously radiate a UV ray to two or more adjacent light emitting device packages 40.

The camera unit 12 may capture an image of the light emitting device package 40 that is radiated with a UV ray emitted by the lighting unit 11. For example, the camera unit 12 may obtain an image of the light emitting device package 40 while the light transmitting resin 150 containing the light conversion material 155 is excited by the UV ray emitted by the lighting unit 11. The image can be obtained by using a photoluminescence effect, a phenomenon in which the light transmitting resin 150 containing the light conversion material 155 emits light by being stimulated by the UV ray emitted by the lighting unit 11.

The image may be analyzed by the test controller 13 to calculate data to be used for determining whether the light emitting device package 40 is defective.

The test controller 13 may set a reference range in each rank by means of the reference gray values in each rank of a to-be-tested object, for example, the light emitting device package 40. For example, the light emitting device package 40 may be divided into the P rank, the R rank, the T rank, and the U rank, according to the difference of the mixing ratio of the light conversion material 155 contained in the light transmitting resin 150. An image of the light emitting device package 40 may have the reference range of the gray values corresponding to each rank. Table 1 below shows the gray values of the light emitting device package 40 in each rank thereof, according to an example embodiment.

TABLE 1

|  | P Rank | R Rank | T Rank | U Rank |
| --- | --- | --- | --- | --- |
| Gray Value (GV) | 66 | 94 | 110 | 143 |
| Reference Range | 56-76 | 86-100 | 103-120 | 133-153 |

The test controller 13 may determine whether gray values calculated from an image generated by the camera unit 12 are outside of a reference range, and may also inspect whether the mixing ratio of the light conversion material 155 contained in the light transmitting resin 150 is abnormal. In some embodiments, when the test controller 13 calculates gray values that are outside of a reference range, the test controller 13 may determine that the mixing ratio of the light conversion material 155 contained in the light transmitting resin 150 is abnormal. For example, the test controller 13 may determine that the mixing ratio is abnormal if the calculated gray value is between reference ranges or is within a reference range different than an expected reference range (i.e., a reference range corresponding to a different rank). The test controller 13 may also determine whether the light emitting device package 40 is defective. For example, the test controller 13 may determine the light emitting device package 40 is defective when the mixing ratio of the light conversion material 155 contained in the light transmitting resin 150 is abnormal.

When the amount of the light conversion material 155 contained in the light transmitting resin 150 is excessive or insufficient in a rank, the light conversion material 155 may be contained therein at an abnormal mixing ratio of the light conversion material 155 rather than at an appropriate mixing ratio thereof, and gray values may thus be changed in an image captured by the camera unit 12. For example, the calculated gray value may vary according to the mixing ratio of the light conversion material 155 contained in the light transmitting resin 150. When the gray values of the image are outside of the reference range in a corresponding rank of the light emitting device package 40, the test controller 13 may determine that an excessive or insufficient amount of the light conversion material 155 is contained in the light transmitting resin 150. For example, the test controller 13 may determine the gray values of the image are outside of the reference range in a corresponding rank of the light emitting device package 40 when the ratio of the light conversion material 155 contained in the light transmitting resin 150 is too high or too low.

For example, when the light transmitting resin 150 containing the light conversion material 155 is dispensed to the light emitting device package 40 at a mixing ratio corresponding to the U rank, in order to manufacture the light emitting device package 40 corresponding to the U rank, the test controller 13 may calculate gray values from an image generated by the camera unit 12, and may compare the calculated gray values with the reference range corresponding to the U rank. When the calculated gray values are greater than an upper limit (e.g., GV: 153) defining the reference range corresponding to the U rank, the test controller 13 may determine that the amount of the light conversion material 155 contained in the light transmitting resin 150 is excessive. Also, when the calculated gray values are less than a lower limit (e.g., GV: 133) defining the reference range corresponding to the U rank, the test controller 13 may determine that the amount of the light conversion material 155 contained in the light transmitting resin 150 is insufficient.

The reference gray values in each rank shown in Table 1 may not be absolute values, and may be changed depending on an optical output of the lighting unit 11. For example, when an optical output of the lighting unit 11 is increased, the test controller 13 may set the reference range to be higher, based on the optical output of the lighting unit 11.

The test apparatus 10, according to an example embodiment, may radiate a UV ray to the light transmitting resin 150 containing the light conversion material 155, which is dispensed to the light emitting device package 40 in order to encapsulate the light emitting device 41. Then the test apparatus 10 may compare an image of the light emitting device package 40, captured when the light transmitting resin 150 is radiated with the UV ray, with reference information according to the mixing ratio of the light conversion material 155, using a photoluminescence effect to rapidly and easily determine whether the mixing ratio is abnormal.

In the related art, whether the mixing ratio of a phosphor is abnormal is determined by applying a current to respective complete light emitting device packages in a test handler process to turn on the light emitting device packages, and then identifying color coordinates of light emitted by LEDs of the light emitting device packages by using a spectroscope. Thus, when a wrong mixing ratio of a phosphor is applied to a manufacturing process or the manufacturing process proceeds with a different mixing ratio of a phosphor due to a worker's mistake, a large number of defects may occur. The reason why the large number of defects may occur is that multistage processes need to be performed from a phosphor dispensing process to the test handler process determining an electrical/optical property of the LEDs, and when the mixing ratio of the phosphor is determined to be inappropriate in the test handler process, a large number of products have been produced already. Further, an additional apparatus, such as a current applying device or a spectroscope, may cause manufacturing costs to be increased and productivity to be reduced.

According to an example embodiment, a vision test may be performed, using the photoluminescence effect immediately after the dispensing process to enable a quick determination and feedback on whether the mixing ratio of the light conversion material 155 is abnormal, thereby preventing the problems of the related art from occurring. For example, the vision test may be performed on the light emitting device package 40 after the dispensing process, but before the light emitting device package 40 proceeds to another, subsequent process.

Figure 3:
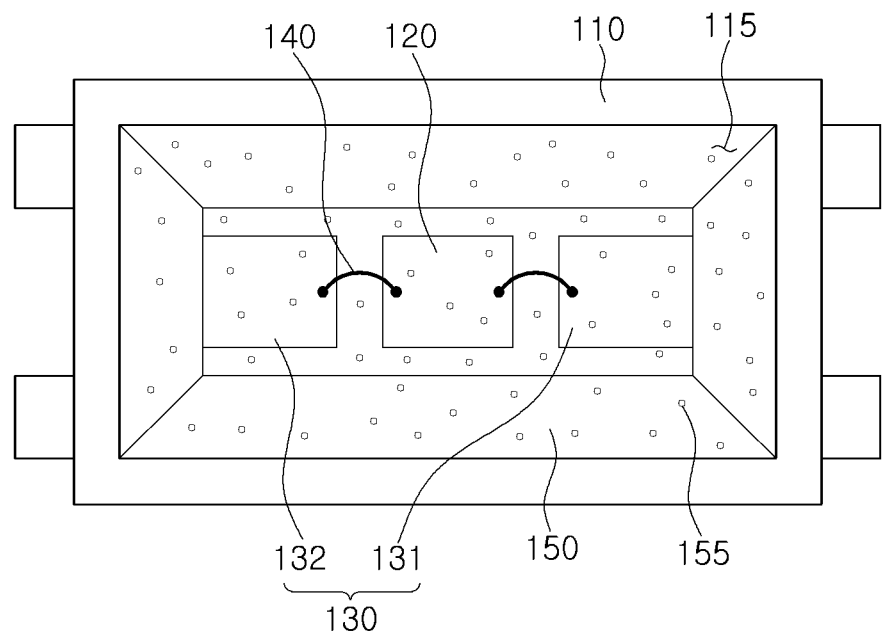
FIG. 3 is a plan view of a light emitting device package that may be manufactured by a manufacturing apparatus for manufacturing a light emitting device package according to an example embodiment.
Figure 4:
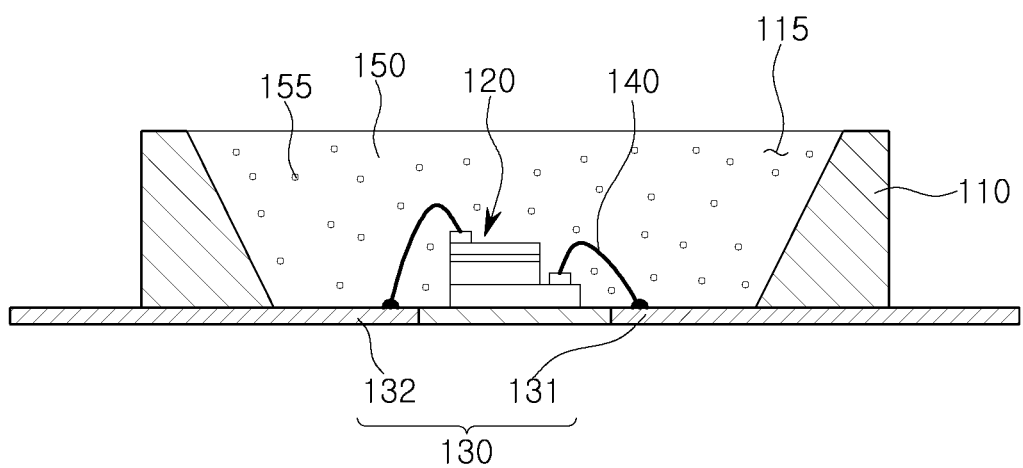
FIG. 4 is a cross-sectional view of the light emitting device package that may be manufactured by the manufacturing apparatus for manufacturing the light emitting device package according to an example embodiment.
Figure 5A:
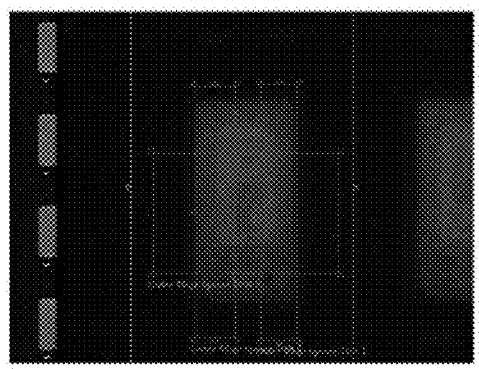
FIGS. 5A through 5D are images of light emitting device packages generated by a test apparatus for testing a light emitting device package according to an example embodiment.
Figure 5B:
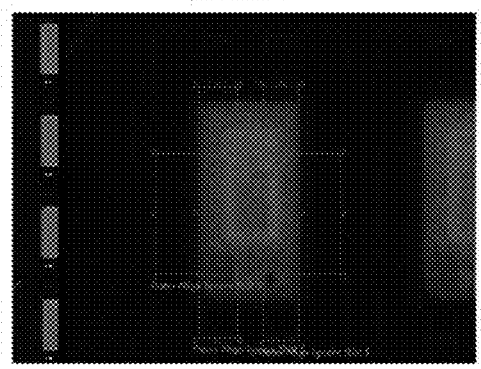
Figure 5C:
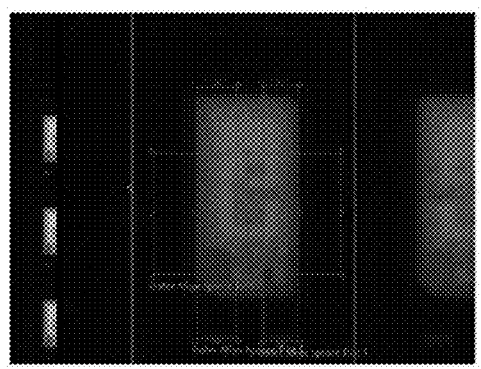
Figure 5D:
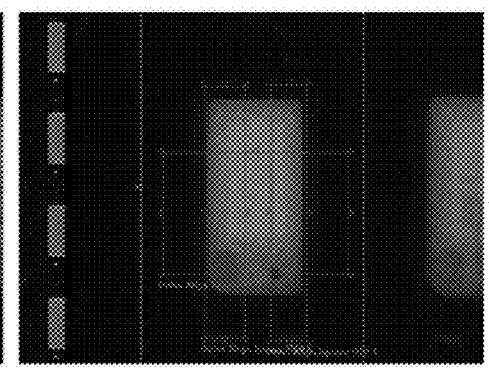

FIG. 3 is a plan view of a light emitting device package that may be manufactured by a manufacturing apparatus for manufacturing a light emitting device package according to an example embodiment. FIG. 4 is a cross-sectional view of the light emitting device package that may be manufactured by the manufacturing apparatus for manufacturing the light emitting device package according to an example embodiment.

Referring to FIGS. 3 and 4, a light emitting device package 100 according to an example embodiment may include a package body 110 providing a mounting space 115, a light emitting device 120 disposed in the mounting space 115, and a lead frame 130 supplying an electrical signal to the light emitting device 120.

The lead frame 130 may include a first lead frame 131 and a second lead frame 132, and the light emitting device 120 and each of the first and second lead frames 131 and 132 may be electrically connected to each other by a wire 140. Alternatively, unlike the example embodiments illustrated in FIGS. 3 and 4, the light emitting device 120 may be electrically connected to the first and second lead frames 131 and 132 in a flip-chip bonding manner.

A portion of the lead frame 130 may protrude externally from the package body 110 to receive an electrical signal. A portion of the lead frame 130 may also be exposed in the mounting space 115 to be connected to an electrode of the light emitting device 120 by the wire 140 or by the flip-chip bonding manner. For example, an electrical signal (e.g., power) may be supplied to portions of the first lead frame 131 and the second lead frame 132 protruding externally from the package body 110, and the first lead frame 131 and the second lead frame 132 may provide the received electrical signal to the electrode of the light emitting device 120 via the wires 140.

After the light emitting device 120 is disposed in the mounting space 115, and then connected to the lead frame 130, the mounting space 115 may be filled with a light transmitting resin 150 containing a light conversion material 155.

The light conversion material 155 may emit light having different wavelengths, such as those emitted by a phosphor or quantum dots, by receiving light emitted by the light emitting device 120. As a material having excellent light transmittance, the light transmitting resin 150 may be dispensed while containing the light conversion material 155 to fill the mounting space 115. The light transmitting resin 150 may also protect the light emitting device 120, the lead frame 130, and the wire 140 in the mounting space 115.

For example, the light emitting device 120, emitting blue light, may be provided in the mounting space 115, and the light conversion material 155, emitting yellow light when excited by the blue light, may be included in the light transmitting resin 150, so that the light emitting device package 100 emitting white light may be implemented.

When the mixing ratio of the light conversion material 155 contained in the light transmitting resin 150 is abnormal, the light emitting device package 100 may not emit light having a desired color. Thus, an apparatus for testing whether the mixing ratio of the light conversion material 155 contained in the light transmitting resin 150 is abnormal may be needed.

As described above with reference to FIGS. 1 and 2, the test apparatus 10, according to an example embodiment, may include a lighting unit 11 configured to emit light having a certain wavelength to the light emitting device package 100, a camera unit 12 configured to capture an image of the light emitting device package 100 emitting the light, and a test controller 13. In some embodiments, the test apparatus 10 and a device dispensing the light transmitting resin 150 may be a single integrated device. Thus, the test apparatus 10 may rapidly identify whether there is a problem with the mixing ratio of the light conversion material 155 contained in the light transmitting resin 150 by dispensing the light transmitting resin 150 to the light emitting device package 100 and, immediately subsequent to the dispensing, inspecting the light transmitting resin 150 using a photoluminescence effect.

FIGS. 5A through 5D are images of light emitting device packages generated by a test apparatus for testing a light emitting device package according to an example embodiment.

First to fourth images 200A to 200D, illustrated in FIGS. 5A through 5D, may be obtained by capturing images of upper surfaces of light emitting device packages 40, coated with light transmitting resins 150 containing light conversion materials 155 in the respective ranks of the light emitting device packages 40, while the light emitting device packages 40 are radiated with a UV ray. For example, the camera unit 12 may capture the first to fourth images 200A to 200D as the lighting unit 11 radiates the light emitting device packages 40 with the UV ray.

It can be seen that when the same UV ray is radiated to the light emitting device packages 40 of the P rank (first image 200A of FIG. 5A having GV: 66), the R rank (second image 200B of FIG. 5B having GV: 94), the T rank (third image 200C of FIG. 5C having GV: 110), and the U rank (fourth image 200D of FIG. 5D having GV: 143), in which the mixing ratios of the light conversion materials 155 are different from each other, degrees of brightness of light emitted by the light conversion materials 155 through excitation thereof by a photoluminescence effect may differ from each other, and thus, gray values of images captured by the camera unit 12 may vary by the above ranks. For example, when UV rays having a same wavelength are applied to light emitting device packages 40 of different ranks, the gray values will vary in accordance with the ranks.

Use of such a photoluminescence effect may allow intuitive determination of whether the mixing ratio of the light conversion material 155 is abnormal, and of whether a light emitting device package 40 to be manufactured can be classified in one rank or another. For example, it can be easily determined that a light emitting device package 40 can be ranked by comparing a reference range with gray values calculated through an image generated while the mixing ratio of a light conversion material 155 has not been determined.

Figure 6:
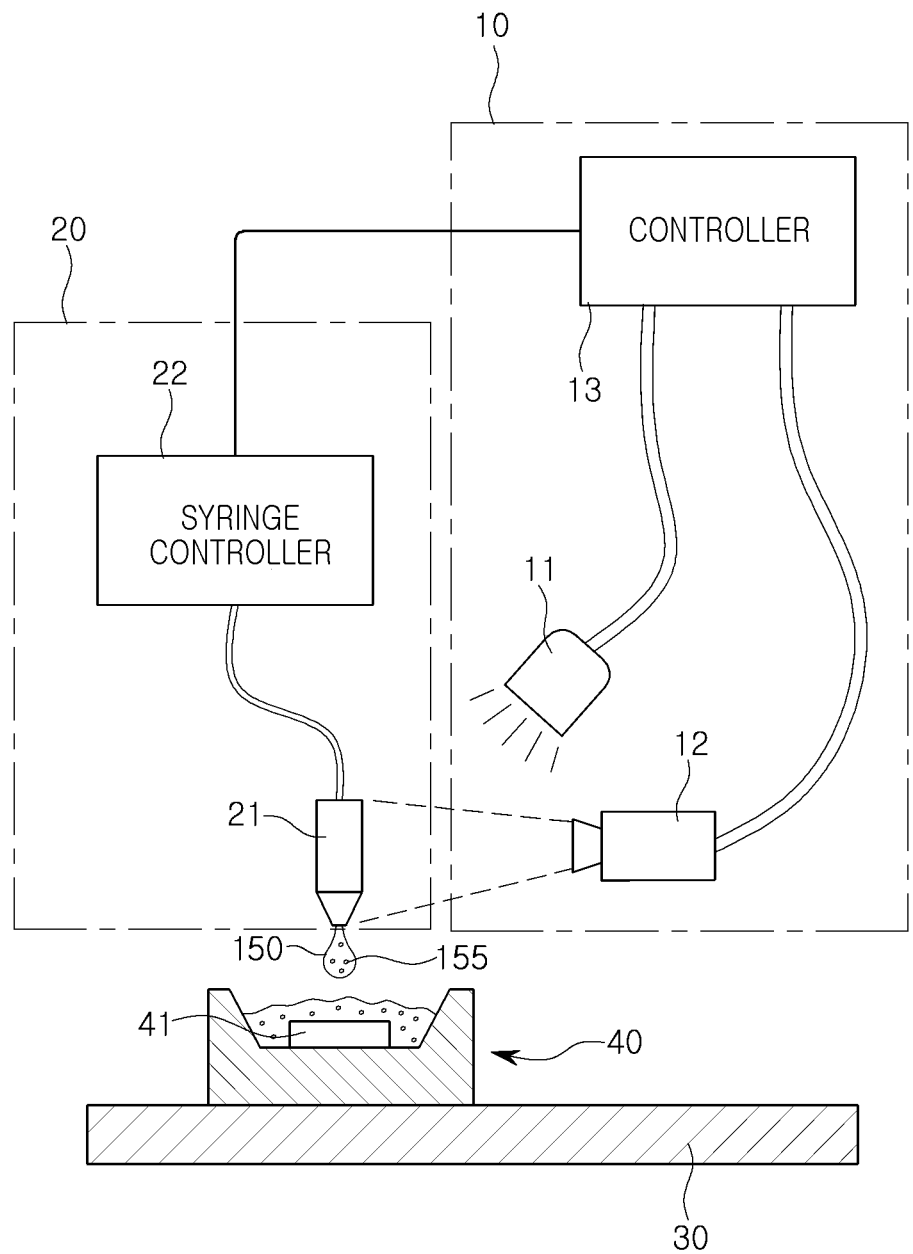
FIG. 6 is a diagram of a manufacturing apparatus for manufacturing a light emitting device package according to an example embodiment.

FIG. 6 is a diagram of a manufacturing apparatus for manufacturing a light emitting device package according to an example embodiment.

Referring to FIG. 6, a manufacturing apparatus 2 for manufacturing a light emitting device package according to an example embodiment may include a resin dispensing unit 20 dispensing a light transmitting resin 150 to a light emitting device package 40, and a test apparatus 10.

The resin dispensing unit 20 may include a syringe 21, dispensing the light transmitting resin 150 in dot units, and a syringe controller 22. The light transmitting resin 150, dispensed to the light emitting device package 40, may include a light conversion material 155, adjusting colors of light emitted by a light emitting device 41.

The test apparatus 10 may test the light transmitting resin 150 containing the light conversion material 155 stored in the syringe 21. For example, the test apparatus 10 may determine whether the light transmitting resin 150 containing the light conversion material 155 is abnormal by using the syringe 21, in which the light transmitting resin 150 containing the light conversion material 155 is stored, as a to-be-tested object.

The test apparatus 10 may radiate light to the syringe 21 by using a lighting unit 11, obtain an image of the syringe 21 using a camera unit 12, and determine whether the syringe 21, the to-be-tested object, is defective by using a test controller 13. The syringe 21 may be determined to be defective when the light conversion material 155 contained in the light transmitting resin 150 within the syringe 21 is determined to be abnormal. For example, the test controller 13 may determine that the light conversion material 155 contained in the light transmitting resin 150 within the syringe 21 is abnormal if a calculated gray value is between reference ranges (e.g., not within a rank-specific reference range), a calculated gray value is within a reference range different than an expected or desired reference range (e.g., within a reference range corresponding to a different rank), multiple calculated gray values of a same image fall within different reference ranges or do not fall within the same reference range, etc.

The lighting unit 11 may have a light source emitting light having a certain wavelength. In some embodiments, the lighting unit 11 may include a UV LED or a blue LED as a light source.

The camera unit 12 may capture an image of the syringe 21 radiated with light emitted by the lighting unit 11. The image, generated by the camera unit 12, may be obtained by capturing a lateral surface of the syringe 21, in which the light transmitting resin 150 containing the light conversion material 155 is stored. In example embodiments, the syringe 21 may have a high light transmittance, allowing UV rays to pass through and radiate the light transmitting resin 150 containing the light conversion material 155 contained in the syringe 21. Likewise, the syringe 21 may allow for the light generated by the radiated light conversion material 155 contained in the light transmitting resin 150 to be detected by the camera unit 12.

The test controller 13 may control operations of the lighting unit 11 and the camera unit 12, and may calculate a gray value from the image generated by the camera unit 12. The test controller 13 may determine whether the light transmitting resin 150 containing the light conversion material 155 is abnormal, based on the calculated gray value. The test controller 13 may also determine whether to replace the syringe 21.

The test controller 13 may test whether gray values calculated from an image generated by the camera unit 12 are uniform throughout the entirety of the syringe 21. For example, when a difference between the calculated gray values occurs in lower and upper regions of the image, the test controller 13 may determine that the distribution of the light conversion material 155 contained in the light transmitting resin 150 is abnormal. For example, the test controller 13 may determine that the calculated gray values for the upper and lower regions are the same when there is a difference of less than 10% between the gray values calculated for the upper and lower regions, and the test controller 13 may determine that the calculated gray values for the upper and lower regions are different when there is a difference of equal to or greater than 10% between the gray values calculated for the upper and lower regions. When the gray values calculated for the upper and lower regions are determined to be substantially the same, then the test controller 13 may determine that the distribution of the light conversion material 155 contained in the light transmitting resin 150 is uniform throughout the entirety of the syringe 21.

Figure 7A:
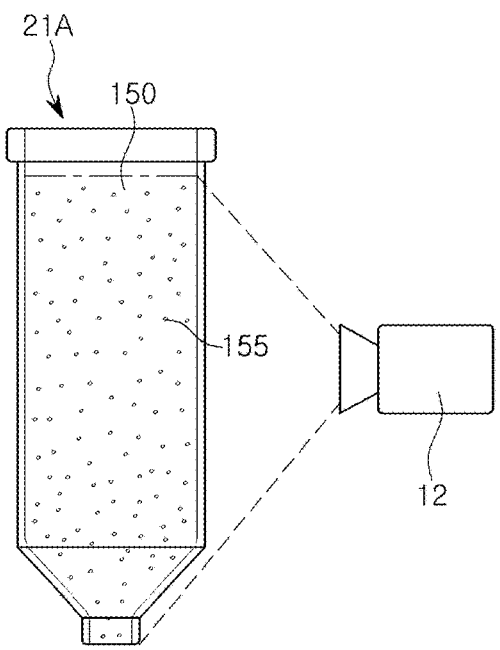
FIGS. 7A and 7B are images of syringes generated by a test apparatus according to an example embodiment.
Figure 7B:
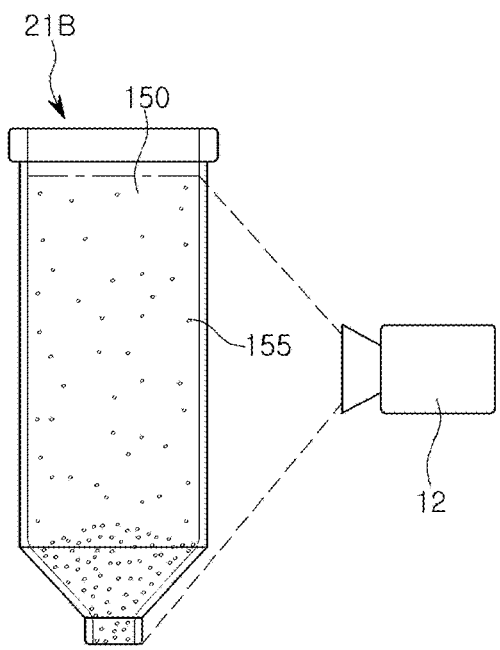

FIGS. 7A and 7B are illustrations of images of syringes generated by a test apparatus according to an example embodiment.

In the example embodiments illustrated in FIGS. 7A and 7B, a first or second syringe 21A or 21B may include a light transmitting resin 150 containing a light conversion material 155. As shown in FIG. 6, test apparatus 10 may include a lighting unit 11 radiating a UV ray in the direction of the syringe 21. For example, the images according to the example embodiments illustrated in FIGS. 7A and 7B may be obtained by the camera unit 12 while the lighting unit 11 radiates a UV ray at the syringe 21.

FIG. 7A is the image of the first syringe 21A, in which light conversion materials 155 are evenly distributed in a light transmitting resin 150. When the camera unit 12 captures the image of the first syringe 21A, a test controller 13 may calculate gray values from the captured image throughout the entirety of the first syringe 21A. When the calculated gray values are uniform over the entire region of the first syringe 21A, the test controller 13 may determine that the first syringe 21A is in a normal state.

FIG. 7B is the image of the second syringe 21B, in which a light conversion material 155 is not evenly distributed in a light transmitting resin 150. When calculated gray values of a lower region of the second syringe 21B are relatively greater than those of an upper region thereof, a test controller 13 may determine that the light conversion material 155 contained in the light transmitting resin 150 has been deposited. For example, in some embodiments, when the test controller 13 calculates relatively lower gray values in the upper region, the test controller 13 may determine that the light transmitting resin 150 has been deposited, at least in part, on the light emitting device package 40, resulting in a reduced volume of light transmitting resin 150 contained in the syringe 21B. The test controller 13 may also determine that the second syringe 21B is defective, and may determine replacement thereof. The test controller 13 may determine the second syringe 21B is defective, for example, when the syringe 21B is empty (partially or completely) or a distribution of the light conversion material 155 in a light transmitting resin 150 is non-uniform. Thus, a worker may replace the second syringe 21B with a new one.

Since the light transmitting resin 150 containing the light conversion material 155 may be stored in the syringe 21 in liquid form, the light conversion material 155 contained in the light transmitting resin 150 may be deposited on a lower side of the syringe 21 over time. When the light conversion material 155 is deposited, the content of the light conversion material 155 contained in the light transmitting resin 150 dispensed to the light emitting device package 40 may not be uniform, resulting in an increase in the distribution of color coordinates of light emitting device packages 40 produced as final products. For example, over time, the light conversion material 155 may migrate within the light transmitting resin 150, resulting in a non-uniform distribution of the light conversion material 155 in the light transmitting resin 150 contained in the syringe 21. In some embodiments, the light conversion material 155 may migrate within the light transmitting resin 150 as a result of gravity or other phenomena. Thus, the syringe, in which the light conversion material is deposited, may need to be replaced with a new one.

Use of such a photoluminescence effect may allow for an intuitive determination of whether the light conversion material 155 is deposited, and a determination of whether a light emitting device package 40 to be manufactured corresponds to any rank. For example, gray values calculated from an image generated while the mixing ratio of the light conversion material 155 has not been determined may allow the syringe 21, in which the light transmitting resin 150 containing the light conversion material 155 is stored, provided to manufacture a light emitting device package 40 corresponding to any rank, to be easily identified. For example, calculating gray values of an image taken of a syringe 21 may allow for identification of the rank of the light transmitting resin 150 containing the light conversion material 155 stored in the syringe 21.

FIGS. 8 through 13 are cross-sectional views of semiconductor light emitting devices that may be applied to a light emitting device package according to example embodiments.

Figure 8:
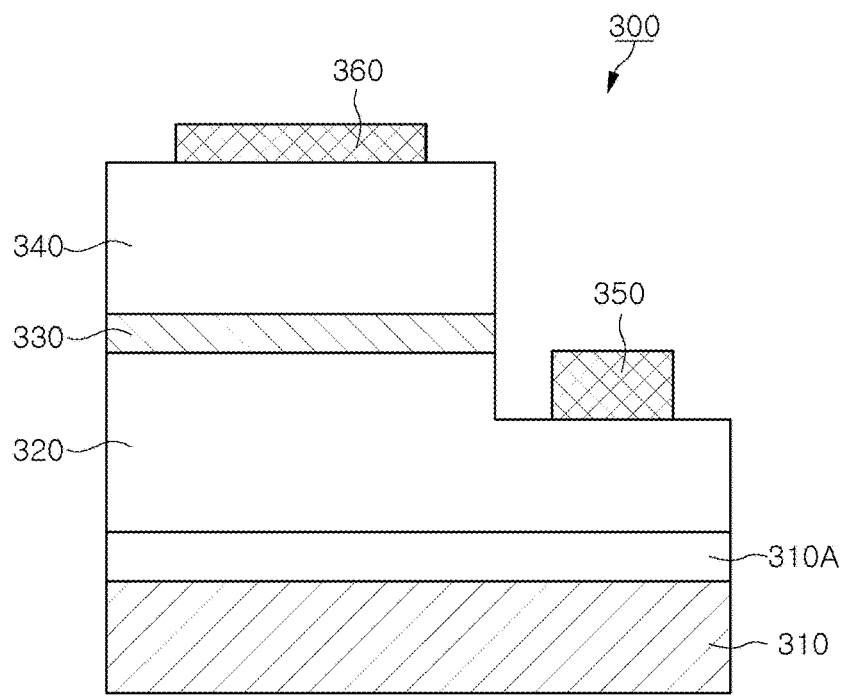
FIGS. 8 through 13 are cross-sectional views of semiconductor light emitting devices that may be applied to a light emitting device package according to an example embodiment.

First, referring to FIG. 8, a semiconductor light emitting device 300 according to an example embodiment may include a growth substrate 310, a first conductive semiconductor layer 320, an active layer 330, and a second conductive semiconductor layer 340. The first conductive semiconductor layer 320 may have a first electrode 350 formed thereon, and the second conductive semiconductor layer 340 may have a second electrode 360 formed thereon. Although not illustrated, the second electrode 360 and the second conductive semiconductor layer 340 may further have an ohmic contact layer selectively disposed therebetween.

At least one of an insulating substrate, a conductive substrate, or a semiconductor substrate may be selected as the growth surface 310, according to various example embodiments. The growth substrate 310 may be, for example, sapphire, silicon carbide (SiC), silicon (Si), $MgAl_2O_4$, MgO, $LiAlO_2$, $LiGaO_2$, or GaN. For epitaxial growth of a GaN material, the same kind of substrate (e.g., a GaN substrate) may be selected as the growth substrate 310, and a sapphire substrate, a silicon carbide (SiC) substrate or the like may be used as a different kind of substrate. When the different kind of substrate is used, a difference between lattice constants of a substrate material and a thin film material may cause a defect, such as a dislocation, to be increased, and a difference between thermal expansion coefficients of the substrate material and the thin film material may result in bending of the different kind of substrate when a temperature changes, and thus the bending may lead to cracking of a thin film. In order to address the above issues, the growth substrate 310, and the first conductive semiconductor layer 320 based on GaN may have a buffer layer 310A disposed therebetween. The buffer layer 310A may adjust the extent of bending of the growth substrate 310 when the active layer 330 is grown to reduce the wavelength distribution of a wafer.

The buffer layer 310A may be formed by using $Al_xIn_yGa_{1-x-y}N$ (0≤x≤1, 0≤y≤1), in particular, GaN, AlN, AlGaN, InGaN, or InGaNAlN, using another material such as $ZrB_2$, $HfB_2$, ZrN, HfN, or TiN, or any combination thereof. The buffer layer 310A may also be formed by combining a plurality of layers or gradually changing compositions thereof.

The first and second conductive semiconductor layers 320 and 340 may include semiconductors doped with n-type and p-type impurities, respectively. The first and second conductive semiconductor layers 320 and 340 are not limited thereto, but may be p-type and n-type semiconductor layers, respectively. For example, each of the first and second conductive semiconductor layers 320 and 340 may include a group III nitride semiconductor layer, such as a material having a composition of $Al_xIn_yGa_{1-x-y}N$ (0≤x≤1, 0≤y≤1, 0≤x+y≤1). The present example embodiment is not limited thereto, and a material, such as an AlGaInP-based semiconductor or an AlGaAs-based semiconductor, may also be used.

Each of the first and second conductive semiconductor layers 320 and 340 may include a single layer structure, and also may have a multilayer structure having different compositions or thicknesses. For example, each of the first and second conductive semiconductor layers 320 and 340 may include a carrier injection layer, able to increase injection efficiency of electrons and holes, and may also include various forms of superlattice structures.

The first conductive semiconductor layer 320 may further include a current diffusion layer in a portion thereof adjacent to the active layer 330. The current diffusion layer may have a structure in which a plurality of layers having different compositions of $In_xAl_yGa_{(1-x-y)}N$, or different impurity contents are repeatedly stacked, or may have an insulating material layer partially formed thereon.

The second conductive semiconductor layer 340 may further include an electron blocking layer in a portion thereof adjacent to the active layer 330. The electron blocking layer may have a structure in which a plurality of layers having different compositions of $In_xAl_yGa_{(1-x-y)}N$ are stacked, or at least one layer having a composition of $Al_yGa_{(1-y)}N$, and the electron blocking layer may prevent electrons from moving to the second conductive semiconductor layer 340 due to having a band gap higher than that of the active layer 330.

In an example embodiment, the first and second conductive semiconductor layers 320 and 340 and the active layer 330 may be manufactured by using a metal organic chemical vapor deposition (MOCVD) apparatus. In order to manufacture the first and second conductive semiconductor layers 320 and 340 and the active layer 330, an organic metal compound gas (e.g., trimethyl gallium (TMG), trimethyl aluminum (TMA) or the like) and a nitrogen-containing gas (e.g., ammonia $NH_3$ or the like) as reaction gases may be supplied to the inside of a reaction vessel in which the growth surface 310 is installed. The growth substrate 310 may remain at a high temperature from 900° C. to 1,100° C. An impurity gas may be supplied, for example, while a nitride gallium-based compound semiconductor is grown on the growth substrate 310. Thus, the nitride gallium-based compound semiconductor may be stacked in an undoped type, an n-type, or a p-type. Silicon (Si) has been well-known as an n-type impurity, and zinc (Zn), cadmium (Cd), beryllium (Be), magnesium (Mg), calcium (Ca), barium (Ba) or the like may be provided as a p-type impurity. In some embodiments, Mg or Zn may be mainly used as a p-type impurity.

The active layer 330, disposed between the first and second conductive semiconductor layers 320 and 340, may have a multiple quantum well (MQW) structure in which quantum well layers and quantum barrier layers are alternately stacked on each other. For example, when the active layer 330 includes a nitride semiconductor, the active layer 330 may have a GaN/InGaN structure, and may also have a single quantum well (SQW) structure. The first or second electrode 350 or 360 may include a material such as silver (Ag), nickel (Ni), aluminum (Al), rhodium (Rh), palladium (Pd), iridium (Ir), ruthenium (Ru), magnesium (Mg), zinc (Zn), platinum (Pt), or gold (Au). The semiconductor light emitting device 300 illustrated in FIG. 8 may have an epi-up (or epi-side up) structure, and may thus be connected to a circuit pattern included in a circuit board in a light emitting device package by a wire or the like.

Figure 9:
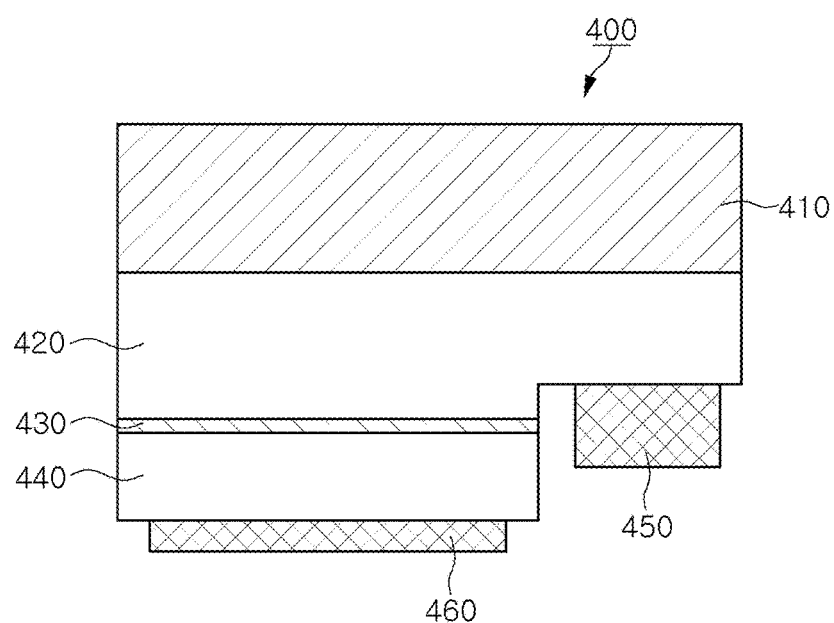

Referring to FIG. 9, a semiconductor light emitting device 400 according to an example embodiment may include a support substrate 410, a first conductive semiconductor layer 420, an active layer 430, a second conductive semiconductor layer 440, a first electrode 450, and a second electrode 460. The semiconductor light emitting device 400 illustrated in FIG. 9 may be bonded to a circuit board of a light emitting device package by flip-chip bonding. Since light generated by the active layer 430 needs to be transmitted to an upper portion thereof, the support substrate 410 may be formed of a material having light transmitting properties.

To reflect light traveling downwardly from the active layer 430, the second electrode 460 may be formed of a material having excellent electrical conductivity and reflectivity. As an example, the second electrode 460 may be formed of at least one of silver (Ag), nickel (Ni), aluminum (Al), rhodium (Rh), palladium (Pd), iridium (Ir), ruthenium (Ru), magnesium (Mg), zinc (Zn), platinum (Pt), and gold (Au).

Figure 10:
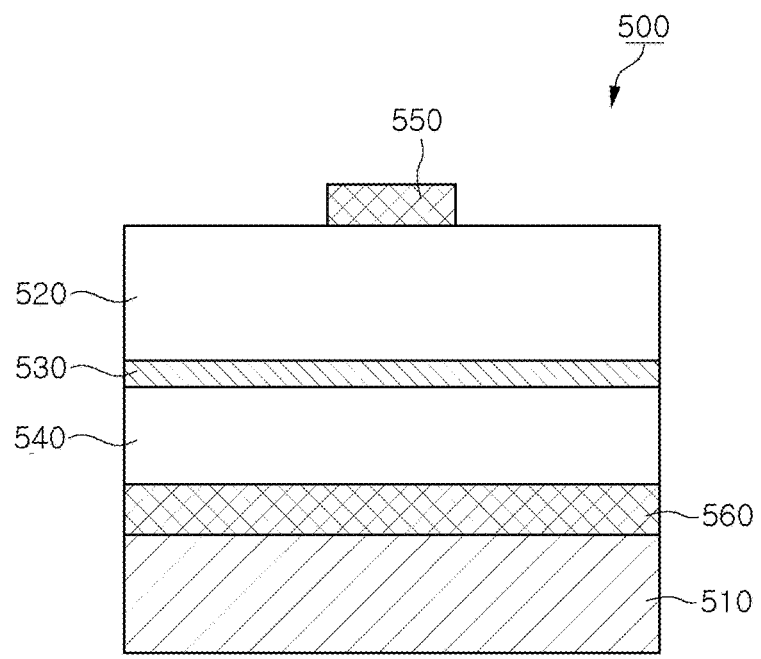

Referring to FIG. 10, a semiconductor light emitting device 500, according to an example embodiment, is illustrated. The semiconductor light emitting device 500 illustrated in FIG. 10 may include a first conductive semiconductor layer 520, an active layer 530, a second conductive semiconductor layer 540, a first electrode 550 bonded to the first conductive semiconductor layer 520, and a second electrode 560 bonded to the second conductive semiconductor layer 540. The second electrode 560 may have a conductive substrate 510 disposed on a lower surface thereof, and the conductive substrate 510 may be directly mounted on a circuit board or the like, configuring a light emitting device package. In the light emitting device package, the conductive substrate 510 may be directly mounted on the circuit board, and the first electrode 550 may be electrically connected to a circuit pattern of the circuit board by a wire or the like.

Similar to the semiconductor light emitting devices 300 and 400 described above, the first and second conductive semiconductor layers 520 and 540 may include n-type and p-type nitride semiconductors, respectively. The active layer 530, disposed between the first and second conductive semiconductor layers 520 and 540, may have an MQW structure in which nitride semiconductor layers having different compositions are alternately stacked, and may selectively have an SQW structure.

The first electrode 550 may be disposed on an upper surface of the first conductive semiconductor layer 520, and the second electrode 560 may be disposed on a lower surface of the second conductive semiconductor layer 540. The active layer 530 of the semiconductor light emitting device 500, illustrated in FIG. 10, may allow light, generated by electron-hole recombination, to be transmitted to the upper surface of the first conductive semiconductor layer 520, on which the first electrode 550 is disposed. Thus, in order for light, generated by the active layer 530, to be reflected in a direction of the upper surface of the first conductive semiconductor layer 520, the second electrode 560 may be formed of a material having a high degree of reflectivity. The second electrode 560 may include at least one of silver (Ag), aluminum (Al), nickel (Ni), chromium (Cr), copper (Cu), gold (Au), palladium (Pd), platinum (Pt), tin (Sn), titanium (Ti), tungsten (W), rhodium (Rh), iridium (Ir), ruthenium (Ru), magnesium (Mg), and zinc (Zn), or alloys thereof.

Figure 11:
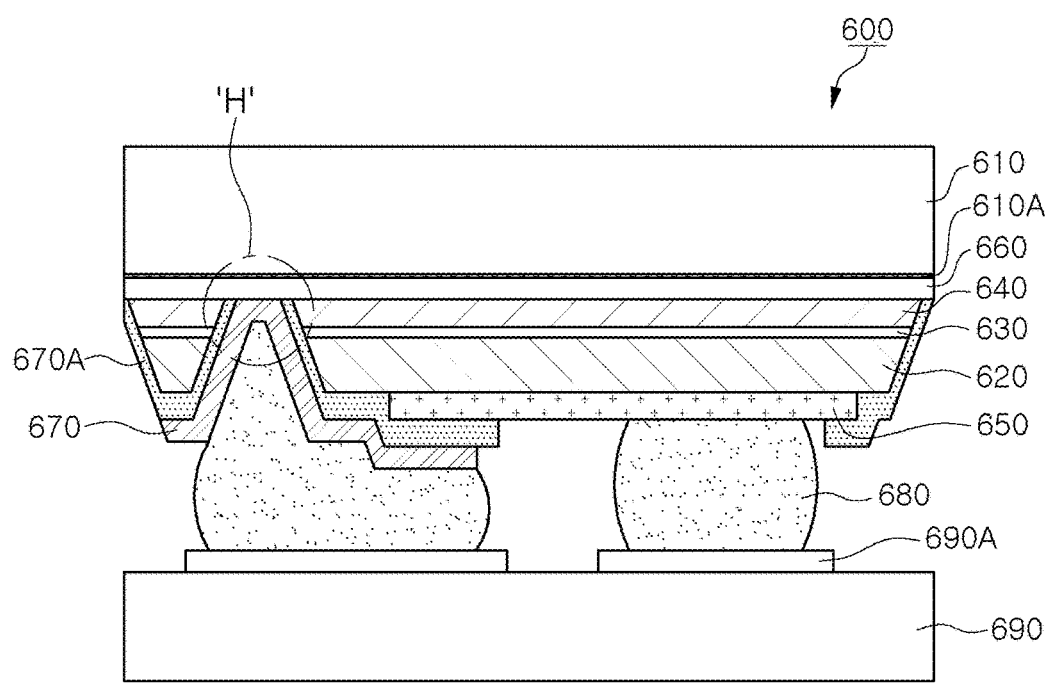

Referring to FIG. 11, a semiconductor light emitting device 600, according to an example embodiment, may include a first conductive semiconductor layer 620, a second conductive semiconductor layer 640, an active layer 630 disposed therebetween, and a first electrode 650 and a second electrode 660 respectively connected to the first conductive semiconductor layer 620 and the second conductive semiconductor layer 640. In an example embodiment, the first and second electrodes 650 and 660 may be respectively disposed on opposite surfaces of the first and second conductive semiconductor layers 620 and 640 while having the first conductive semiconductor layer 620, the active layer 630, and the second conductive semiconductor layer 640 interposed therebetween. The second electrode 660 may have a support substrate 610 bonded thereto by a bonding layer 610A to support the semiconductor light emitting device 600.

The light emitting device 600, according to an example embodiment, may further include a connecting electrode 670 as an electrode element connected to the second electrode 660. The connecting electrode 670 may be connected to the second electrode 660 by a through hole H, formed by removing regions of at least the first conductive semiconductor layer 620, the active layer 630, and the second conductive semiconductor layer 640. The through hole H may allow at least a region of the second electrode 660 to be exposed, and the second electrode 660 and the connecting electrode 670 may be connected to each other in the exposed region. The connecting electrode 670 may be formed along side walls of the through hole H. An insulating layer 670A may be disposed between the connecting electrode 670 and the side walls of the through hole H to prevent the connecting electrode 670 from being electrically connected to the active layer 630 and the first conductive semiconductor layer 620. The insulating layer 670A may also be formed on side surfaces of the first conductive semiconductor layer 620, the active layer 630, and the second conductive semiconductor layer 640 as a passivation layer for the light emitting device 600. The insulating layer 670A may include a silicon oxide or a silicon nitride.

The electrode structure mentioned above may be applied more efficiently when the first and second conductive semiconductor layers 620 and 640 are n-type and p-type nitride semiconductor layers, respectively. The p-type nitride semiconductor layer may have a higher level of contact resistance than the n-type nitride semiconductor layer, and obtaining ohmic contact may thus be difficult. However, in the example embodiment illustrated in FIG. 11, the second electrode 660 may be disposed over the entire surface of the support substrate 610 to secure a sufficient contact region between the second conductive semiconductor layer 640 and the second electrode 660, thus obtaining ohmic contact with the p-type nitride semiconductor layer.

The semiconductor light emitting device 600, according to the example embodiment illustrated in FIG. 11, may have a flip-chip structure in which light may be transmitted in a direction of the support substrate 610. For example, the first electrode 650 and the connecting electrode 670 may be electrically connected to a circuit pattern 690A of a circuit board 690 through a solder bump 680 or the like. Thus, the first electrode 650 may include an electrode material having a high degree of reflectivity, as well as ohmic contact characteristics. The second electrode 660 and the support substrate 610 may have a high degree of light transmitting properties. For example, the first electrode 650 may include a material such as silver (Ag), nickel (Ni), aluminum (Al), rhodium (Rh), palladium (Pd), iridium (Ir), ruthenium (Ru), magnesium (Mg), zinc (Zn), platinum (Pt), or gold (Au). The second electrode 660 may be a light transmitting metal such as nickel (Ni) or gold (Au), or a transparent conductive oxide or nitride, such as an indium tin oxide (ITO). The support substrate 610 may be a glass substrate or a substrate formed of a light transmitting polymer resin.

Figure 12:
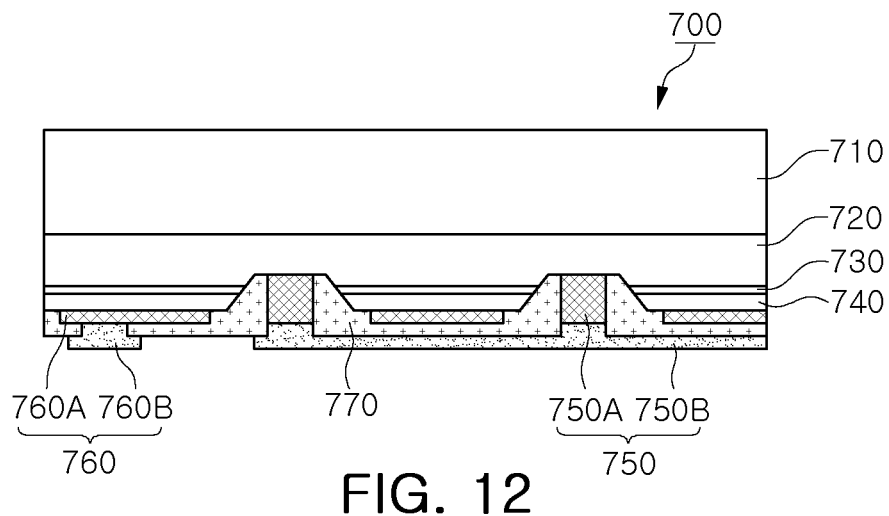

Referring to FIG. 12, a semiconductor light emitting device 700 according to an example embodiment is illustrated. The semiconductor light emitting device 700 may include a first conductive semiconductor layer 720, an active layer 730, and a second conductive semiconductor layer 740 sequentially stacked on a surface of a substrate 710, a first electrode 750, and a second electrode 760. The semiconductor light emitting device 700 may also include an insulator 770. The first electrode 750 may include a first contact electrode 750A and a first connecting electrode 750B, and the second electrode 760 may include a second contact electrode 760A and a second connecting electrode 760B. Regions of the first and second contact electrodes 750A and 760A exposed by the insulator 770 may be connected to the first and second connecting electrodes 750B and 760B, respectively.

The first contact electrode 750A may be provided as a conductive via passing through the second conductive semiconductor layer 740 and the active layer 730, to be connected to the first conductive semiconductor layer 720. The second contact electrode 760A may be connected to the second conductive semiconductor layer 740. The conductive via may be provided as a plurality of conductive vias in a single light emitting device region.

The first and second contact electrodes 750A and 760A may be formed on the first and second conductive semiconductor layers 720 and 740, respectively, by depositing conductive ohmic materials on the first and second conductive semiconductor layers 720 and 740. The first and second contact electrodes 750A and 760A may include at least one of silver (Ag), aluminum (Al), nickel (Ni), chromium (Cr), copper (Cu), gold (Au), palladium (Pd), platinum (Pt), tin (Sn), titanium (Ti), tungsten (W), rhodium (Rh), iridium (Ir), ruthenium (Ru), magnesium (Mg), and zinc (Zn), or alloys thereof. In addition, the second contact electrode 760A may function to reflect light transmitted from the active layer 730 to a lower portion of the semiconductor light emitting device 700.

The insulator 770 may have an open region exposing at least a portion of each of the first and second contact electrodes 750A and 760A, and the first and second connecting electrodes 750B and 760B may be connected to the first and second contact electrodes 750A and 760A, respectively. The insulator 770 may be deposited to have a thickness from 0.01 μm to 3 μm at a temperature of 500° C. or below by an $SiO_2$ or SiN chemical vapor deposition (CVD) process. The first and second electrodes 750 and 760 may be mounted on a light emitting device package in flip-chip form.

The first and second electrodes 750 and 760 may be electrically isolated from each other by the insulator 770. The insulator 770 may be any material having electrically insulating characteristics, but may be, for example, a material having a low degree of light absorption to prevent light extraction efficiency of the semiconductor light emitting device 700 from deteriorating. For example, a silicon oxide, such as $SiO_2$, $SiO_xN_y$ or the like, and a silicon nitride, such as $Si_xN_y$ or the like, may be used. In some embodiments, a light-reflective structure may be formed by dispersing a light-reflective filler in a light transmitting material.

The substrate 710 may have a first surface and a second surface opposing each other, and at least one of the first and second surfaces may also have an unevenness structure formed thereon. An unevenness structure that may be formed on a surface of the substrate 710 may be constructed by etching a portion of the substrate 710, and may include the same kind of material as the substrate 710, or a different kind of material from the substrate 710. For example, an unevenness structure may be formed at an interface between the substrate 710 and the first conductive semiconductor layer 720, to allow a path of light, emitted by the active layer 730, to vary. Thus, a light absorption rate of the first conductive semiconductor layer 720 may be reduced, and a light scattering ratio thereof may be increased, resulting in an increase in light extraction efficiency of the semiconductor light emitting device 700. The substrate 710 and the first conductive semiconductor layer 720 may also have a buffer layer disposed therebetween.

Figure 13:
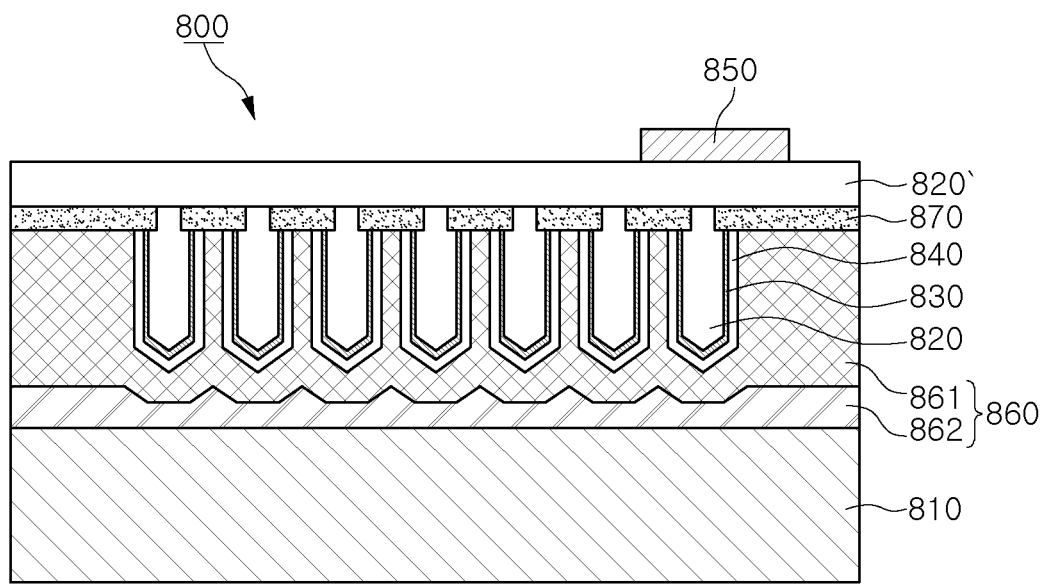

Referring to FIG. 13, a semiconductor light emitting device 800, according to an example embodiment, may have a light emitting nanostructure. The semiconductor light emitting device 800 may include a base layer 820' including a first conductive semiconductor material, a mask layer 870 provided on the base layer 820' and having a plurality of openings, and nanocores 820 formed in the openings of the mask layer 870. Each of the nanocores 820 may have an active layer 830 and a second conductive semiconductor layer 840 provided on the active layer 830. The nanocores 820, the active layer 830, and the second conductive semiconductor layer 840 may form the light emitting nanostructure.

The second conductive semiconductor layer 840 may have a second contact electrode 861 provided thereon, and the second contact electrode 861 may have a second connecting electrode 862 provided on a surface thereof. The second contact electrode 861 and the second connecting electrode 862 may be provided as a second electrode 860. The second electrode 860 may have a support substrate 810 bonded to a surface thereof, and the support substrate 810 may be a conductive substrate or an insulating substrate. When the support substrate 810 is conductive, the support substrate 810 may be directly mounted on a circuit board of a light emitting device package. The base layer 820', including the first conductive semiconductor material, may have a first electrode 850 provided thereon. The first electrode 850 may be connected to a circuit pattern included in the circuit board of the light emitting device package by a wire or the like.

As set forth above, according to example embodiments, a test apparatus and a manufacturing apparatus of a light emitting device package may determine whether the mixing ratio of a light conversion material contained in a light transmitting resin is abnormal by obtaining an image of a light emitting device package by radiating light having a certain wavelength to the light emitting device package having the light transmitting resin containing the light conversion material, calculating gray values from the obtained image, and determining whether the calculated gray values are outside of a reference range. Thus, whether the mixing ratio of the light conversion material contained in the light transmitting resin is abnormal may be rapidly and efficiently determined without using an expensive device.

While exemplary embodiments have been shown and described above, it will be apparent to those skilled in the art that modifications and variations could be made without departing from the scope of the present inventive concepts, as defined by the appended claims.

What is claimed is:

1. A method of testing an object, comprising:
    radiating light from a lighting unit to a test object having a light transmitting resin containing a light conversion material;
    obtaining an image of the test object by a camera unit while the light transmitting resin is receiving light emitted by the lighting unit; and
    determining whether the test object is defective by calculating gray values corresponding to the image obtained by the camera unit.

2. The method of claim 1, wherein the test object is a light emitting device package having a light emitting device encapsulated by the light transmitting resin containing the light conversion material, the method further comprising:
    setting a reference range of per-rank gray values of the light emitting device package; and
    determining whether the light emitting device package is defective according to whether the calculated gray values are included in the reference range.

3. The method of claim 2, further comprising:
    determining that a mixing ratio of the light conversion material contained in the light transmitting resin is abnormal based on the calculated gray values being outside of the reference range.

4. The method of claim 2, further comprising:
    determining that an amount of the light conversion material contained in the light transmitting resin is excessive based on the calculated gray values being greater than an upper limit of the reference range.

5. The method of claim 2, further comprising:
    determining that an amount of the light conversion material contained in the light transmitting resin is insufficient based on the calculated gray values being less than a lower limit of the reference range.

6. The method of claim 2, wherein setting the reference range comprises setting the reference range based on an optical output of the lighting unit.

7. The method of claim 1, wherein the test object is a light transmitting syringe storing the light transmitting resin containing the light conversion material, the method further comprising:
    determining whether the light transmitting syringe is defective according to whether the calculated gray values are uniform over the entire region of the light transmitting syringe.

8. The method of claim 7, further comprising:
    determining that a distribution of the light conversion material contained in the light transmitting resin is abnormal based on first gray values calculated for a lower region of the light transmitting syringe being different from second gray values calculated for an upper region of the light transmitting syringe.

9. The method of claim 7, further comprising:
    determining that the light conversion material contained in the light transmitting resin is deposited on the tested object when first gray values calculated for a lower region of the light transmitting syringe are greater than second gray values calculated for an upper region of the light transmitting syringe.

10. A method of manufacturing comprising:
    providing a light emitting device package;
    dispensing a light transmitting resin containing a light conversion material to the light emitting device package; and
    obtaining an image by radiating light having a certain wavelength onto the light emitting device package having the light transmitting resin dispensed thereon;
    calculating gray values from the obtained image;
    comparing the calculated gray values with a reference range of gray values set according to a rank of the light emitting device package; and
    determining whether the light emitting device package is defective based on the comparing of the calculated gray values with the reference range of gray values.

11. The method of claim 10, further comprising:
    determining that a mixing ratio of the light conversion material contained in the light transmitting resin is abnormal based on the calculated gray values being outside of the reference range.

12. The method of claim 10, further comprising:
    determining that an amount of the light conversion material contained in the light transmitting resin is excessive based on the calculated gray values being greater than an upper limit of the reference range.

13. The method of claim 10, further comprising:
    determining that an amount of the light conversion material contained in the light transmitting resin is insufficient based on the calculated gray values being less than a lower limit of the reference range.

14. The method of claim 10, further comprising:
    providing the light transmitting resin containing the light conversion material on the light emitting device package in dots.

15. The method of claim 14, wherein the calculated gray values include first and second gray values, the method further including:
    determining that a distribution of the light conversion material contained in the light transmitting resin is abnormal based on the first gray values calculated for a lower region of a syringe differing from and the second gray values calculated for an upper region of the syringe.

16. A method for testing comprising:
    radiating light to an object having a light transmitting resin containing a light conversion material;
    obtaining an image of the object while the light conversion material is excited by the light radiated by a lighting unit;
    calculating at least one gray value corresponding to the image;
    comparing the at least one gray value with a reference range of gray values set according to a rank of the object; and
    determining whether the at least one gray value is within the reference range of gray values.

17. The method of claim 16, further comprising:
    determining that a mixing ratio of the light conversion material contained in the light transmitting resin is abnormal based on the at least one gray value being outside of the reference range.

18. The method of claim 16, wherein the at least one gray value includes first gray values calculated for an upper region of a syringe and second gray values calculated for a lower region of the syringe, the method further comprising:
    determining that a distribution of the light conversion material contained in the light transmitting resin is abnormal based on the first gray values being different than the second gray values.

19. The method of claim 16, wherein the at least one gray value includes first gray values calculated for an upper region of a syringe and second gray values calculated for a lower region of the syringe, the method further comprising:
    determining that the light conversion material contained in the light transmitting resin is deposited on the object when the first gray values are greater than the second gray values.

20. The method of claim 16, further comprising:
    determining that the object is defective when a gray value of the at least one gray value is determined not to be within the reference range of gray values.

* * * * *